United States Patent
Bretz

(10) Patent No.: US 6,932,840 B1
(45) Date of Patent: Aug. 23, 2005

(54) IMPLANT DEVICE

(75) Inventor: Phillip D. Bretz, Palm Desert, CA (US)

(73) Assignee: Absolute Breast Solutions, Palm Springs, CA (US)

( * ) Notice: Subject to any disclaimer, the term of this patent is extended or adjusted under 35 U.S.C. 154(b) by 25 days.

(21) Appl. No.: 10/935,171

(22) Filed: Sep. 8, 2004

(51) Int. Cl.[7] .................................. A61F 2/12
(52) U.S. Cl. ................. 623/8; 623/23.34; 623/11.11
(58) Field of Search ................. 623/7.8, 11.11, 623/23.64; 524/800

(56) References Cited

U.S. PATENT DOCUMENTS

| | | | | |
|---|---|---|---|---|
| 3,934,274 A | * | 1/1976 | Hartley, Jr. ................. | 623/8 |
| 4,610,690 A | * | 9/1986 | Tiffany ........................ | 623/8 |
| 4,731,081 A | * | 3/1988 | Tiffany et al. ............... | 623/8 |
| 4,995,882 A | * | 2/1991 | Destouet et al. ............ | 623/8 |
| 5,002,071 A | * | 3/1991 | Harrell ........................ | 128/897 |
| 5,500,017 A | * | 3/1996 | Bretz et al. .................. | 623/8 |
| 6,368,658 B1 | * | 4/2002 | Schwarz et al. ............ | 427/2.15 |
| 6,558,315 B1 | * | 5/2003 | Kuyava ........................ | 600/40 |
| 2004/0010077 A1 | * | 1/2004 | Nile et al. ................... | 528/800 |
| 2004/0224406 A1 | * | 11/2004 | Altman et al. ............. | 435/395 |

\* cited by examiner

Primary Examiner—David J. Isabella
(74) Attorney, Agent, or Firm—Dennison, Schultz, Dougherty & MacDonald

(57) ABSTRACT

A human or animal implant device including a first, inner sealed silicone sheet sac, a second, intermediate sealed silicone sheet sac completely surrounding the first, inner sac, and a third, outer sealed silicone sheet sac completely surrounding the second sac. Each sac has a coating of beeswax on inner and outer walls thereof, and the first, inner sac is filled with a substantially sterile liquid material, preferably of viscosity at least 15 cp. The second, intermediate sac and the third, outer sac are filled with aqueous saline solution.

8 Claims, 1 Drawing Sheet

IMPLANT DEVICE

BACKGROUND OF THE INVENTION

The invention relates to the field of implants used in human surgery to reconstruct or augment various body parts, in particular breast implants.

In dealing with breast augmentation, four undesirable side effects have plagued researchers and surgeons for over forty years. These side effects are:

1) an unsafe implant. Safety arguably is the most important factor facing the medical implant community and to date there has not been an ideally safe implant eliminating both short and long term toxic local and systemic outcomes such as autoimmune diseases and silicone related inflammations.

2) gel/saline "bleed". This "bleeding" of fill material causes distasteful feel and an unacceptable cosmetic appearance (such as a deflated saline implant requiring another surgery) and local silicone related inflammations;

3) capsular formation. Scar tissue capsule formation usually forms around the implant frequently causing a rock hard implant with further distasteful feel, dislocation and pain, often times resulting in subsequent surgeries to cure or diminish the complicating factors of such scar tissue formation.

4) loss of sex appeal. The capsular formation referred to above results ultimately in the loss of the desired and hoped for added sex appeal that cosmetic surgery usually promises.

More specifically, unsafe implants and in particular breast implants have caused a wide, seemingly endless array of catastrophic outcomes. The United States Food and Drug Administration (FDA) decreed in early 2004 the continued clinical hold from the market of silicone implants for first time breast implant patients. The FDA called for extensive re-evaluation and further testing of the potential for rupture, thought to cause systemic disorders. Included in this list of clinical problems are silicone mastitis and migration of free silicone into major organ systems such as the liver. This potential continues with every current implant offered.

Numerous complications related to the use of silicone are known and include the use of free silicone injections in the early 1960's, which ultimately resulted in coalescing of the silicone into silicone mastitis (hard lumps throughout the breast tissue) making the diagnosis of invasive cancer of the breast most difficult and resulting in a near impossible mammogram to read. Following these early attempts of free silicone injection came silicone gel encased in a silicone sac. All these silicone implants, although having a so called "sexy feel," produced gel bleed or outright rupture in a number of cases, resulting locally in hard lumps in the breast as well as systemic migration of the silicone into major organ systems such as the liver. Some studies have shown not only the development of serious systemic side effects such as scleraderma type autoimmune disorders but also the development of various antibodies against the women's own collagen. Further, in some patients, "leaching" of silicone from the wall of an intact implant by select macrophages produced the same undesirable and dangerous systemic side effects without implant rupture.

A number of revisions to the silicone sac were proposed, including single and double lumens. The double lumen implant with silicone residing in the inner sac surrounded by a saline filled outer sac was thought to be the answer to the above problems, and indeed, the double lumen implant offered for the most part a continually soft feel implant long term and without as much capsule formation as opposed to the single lumen. However, over the years it was learned that the internal sac was prone to rupture on occasion, which now meant that the patient and surgeon worried about the integrity of the remaining outer sac, and if it should be replaced (accounting for another expensive operation with its own associated risks), since the previous double lumen implant was now a single lumen sac.

Further investigation into the problems of silicone use led to the development of saline single lumen sacs. This development eliminated for the most part the widespread effects of free silicone in human tissue, but it did not have the safety of the double lumen which afforded some protection from a ruptured implant and consequent spilling the contents of the sac into the tissue. While free saline in the tissue did not result in the same problems as free silicone, the single lumen saline sac at times resulted in a totally deflated implant and the necessity of another operation with its expense and risk. Further, the reported incidence of deflation as reported by Grossman, "The Current Status of Augmentation Mammaplasty," in Plastic and Reconstructive Surgery 52:1 (1973), reaches as high as 76%. This saline bleed results in "crinkling" of the sac and in some case "sloshing" of the remaining saline in a less then filled implant, and further results in an extremely distasteful feel to the now crippled implant. The result is A decidedly un-sexy implant, exactly the opposite result from what the patient wanted, thereby defeating the purpose of undergoing the cosmetic procedure.

A review of the patent implant literature finds several patents that discuss the problem of capsule formation, specifically U.S. Pat. Nos. 4,955,907, 4,731,081, 5,571,183, 5,207,709, 5,354,338, 4,428,082, and 4,298,998. While these patents propose solutions to capsule formation, all have several common denominators which have the potential of making them unsuitable for resolving this problem in human beings. For example, U.S. Pat. No. 4,298,998 discloses causing a capsule to form at a predetermined, controlled distance from the surface of the implant, thus resulting in the same capsule but at a different location. The end result clinically appears to be a hard capsule for the patient and not resolving the problem.

Similarly, the implant of U.S. Pat. No. 5,207,709 includes a plurality of fin projections extending from the outer surface arrayed in a basket weave-like, herringbone-like, or other suitable pattern to create a sinuous path for collagen formation around the implanted device. It appears that this implant actually creates or invites collagen formation again in another location around the implant, again not resolving the problem. Still other patents relate to the implant being surrounded by a medical grade elastomer or as U.S. Pat. No. 4,944,749 states, a viscous gel coating with the membranes constructed of a suitable material such as medical grade silicone rubber which does not react with human tissue. The outer membrane contains an amount of viscous gel, for example a silicone rubber gel of medical grade silicone. It appears in the end that this patent still has a silicone tissue interface that has accounted for problems.

U.S. Pat. No. 4,610,690 is directed to an implant with a lubricious layer of an acrylamide polymer radiation bonded to at least one wall surface of a silicone shell or bag. Potential long-term effects in human beings of an acrylamide polymer interface are not discussed.

All these aforementioned patents continue to have unnatural chemicals as the interface with human tissue, which is exactly what patients do not want in their body.

U.S. Pat. No. 4,995,882 proposed an organic fill solution to the implant problem. This implant proposed the use of a triglyceride fill substance such as peanut oil or sunflower seed oil as the ideal filler. Although some were implanted in Europe, they were never authorized for implantation in the United States and were subsequently taken off the market worldwide because of various problems.

In U.S. Pat. No. 5,500,017 (incorporated herein by reference), of which the Applicant is a co-inventor, it was proposed to use a sugar syrup, preferably honey, to fill the implant sac. The use of honey is thought to present the following advantages:

1) safety. Since honey is organic, natural and edible, and bio-compatibility studies show low toxicity associated with honey-filled breast implants even with free honey injected into living tissue;

2) honey-filled breast implants, because of the viscosity of honey (at least 15 cp), have the feel of a natural breast which are mimicked by silicone;

3) the United States Department of Agriculture has extensive studies and regulations regarding grades of honey.

Applicant found however, that the use of honey did present some problems. While every other implant had a problem with gel/saline "bleed," the honey-filled implant had a problem with interstitial body fluid migrating into the sac. This migration is caused by an osmotic gradient whereby the viscosity of the honey inside the sac forces less viscous interstitial fluid into the sac to create an equilibrium. This migration results in an incremental increase in the weight of the implant, which made its ultimate use prohibitive. Also, while honey is safe for most individuals, there are some persons who may be allergic to honey, making a honey-filled sac unsuitable in this sub-population.

SUMMARY OF THE INVENTION

It is therefore an object of the invention to provide a natural implant which does not present problems with allergies, which insures against leakage and which does not result in capsule formation.

It is a further object of the invention to provide an implant which prevents both inflation and deflation of the sac in use, and which avoids over-inflation of the sac by the implanting surgeon.

To achieve these and other objects, the invention modifies both the sac and the filler of an implant.

In order to prevent capsule formation and transfer of liquid through the sac walls, the walls of the sac are coated with beeswax. Moreover, the filler material according to the invention is an ultrafiltered natural liquid of the correct viscosity, in particular honey, blue agave or aloe vera. Finally, the use of a triple lumen implant reduces the risk that rupture of the implant will result in the filling contacting human tissue.

The first problem of interstitial fluid flowing into the implant causing a weight gain was solved utilizing beeswax, the solution used in nature to protect honey over long periods of time. Through experimentation, it was found that if the sac is coated after formation, the beeswax coated onto the outer surface would crack and chip off easily. Unexpectedly, it was determined that this problem could be avoided by coating both sides of a silicone sheet before forming the sac by dipping the sheet into melted wax. After drying the beeswax on the surface of the silicone sac, the wax bonded well to the surface, and the sac remained extremely supple and pliable. With the silicone sac encased in beeswax, the silicone never comes into contact with human tissue, thereby preventing capsule formation because of the natural and inert nature of the beeswax. Electron microscopy of the coated sac has demonstrated that this technique melds the wax into both the outer and internal walls of the sac and permits the sac to bend in a very natural, pliable and permanent manner.

The thickness of the beeswax coating on each surface of the silicone sac is in the range of about 0.01 to 1 mm.

By coating the silicone sac with beeswax, the problem of influx and outflow of fluids through the sac wall is eliminated, while maintaining an ideal weight and feel. Further, this coating prevents what is known as "self-abrasion injury" of the sac that is caused by the fluid bleeding out and the inner walls of a double lumen sac rubbing against each other, which causes a weak point in the sac and further bleeding or rupture.

Beeswax has been used for many decades in the operating theatre by orthopedic surgeons to plug cracks in bone and by cardiac surgeons to plug bleeding sites in the sternum prior to chest closure. A search of the medical research literature has found no reported allergy, or any constant inflammatory response including any type of capsule formation. This coating therefore solves one of the most devastating problems of implant surgery, that of capsule formation and its accompanying hard implant feel and subsequent body disfigurement. The coating of the implant in this manner maintains a soft supple, natural interface with living tissues.

Clinical animal trials were conducted to study the incidence of capsule formation with standard and beeswax coated implants. Applicant implanted uncoated silicone sac segments and beeswax coated sac segments into the subcutaneous abdominal layer of goats. Two of each implants were implanted and time was allowed for maturing of the surgical site to investigate the possible development of capsular formation. It was confirmed that the beeswax coated sac segments had no clinical or microscopic evidence of capsule formation.

The next problem to overcome was the allergy to honey or its enzymes demonstrated by some persons, rendering them non-candidates for honey-filled breast implants. We solved this dilemma in two ways. First, the Grade A honey was submitted to a special ultra-filtration which effectively removed all particulate matter down to 20 thousand molecular weight. This special process not only removed all visible particulate matter harvested with the honey from the field but also removed all enzymes which might cause allergic reactions. The resultant honey is called "high-tech" honey by Applicant, and the filtration process is thought to effectively remove all allergens from the honey fill material.

The other method used to eliminate the potential allergic reactions to honey was to utilize other naturally occurring substances of the proper viscosity, which are plant rather that animal products. The viscous fluids selected for this purpose were extracts of blue agave and aloe vera. Blue agave is the plant from which tequila is made, and carries none of the potential animal allergens of honey because of its plant origin. It too can be ultra-filtered into "high tech" agave. Likewise, aloe vera is a plant with healing properties well known in the medical community; it has been used in thousands of breast radiation patients daily across the country for decades. This product can also be ultra-filtered into "high tech" aloe.

An animal clinical trial was conducted to determine any potentially harmful effects of ultra-filtered blue agave and aloe vera. Amounts of up to 100 ml of ultra-filtered blue agave and aloe vera were injected into the abdominal subcutaneous layer of goats to simulate the rupture of an implant. Enough time was allowed to pass to determine if there were toxic side effects associated with these materials, and the animals were humanely re-examined at the injection sites, to determine any local inflammation or overt capsule formation. The tissue removed was studied both grossly and microscopically. The results demonstrated the non-inflammatory nature of "high tech" agave and aloe injections.

Lastly, a triple lumen implant was developed to improve the safety of the currently used implants. The inner sac "vault" would be filled with one of the ultra-filtered materials of the invention, or mixtures thereof since all are water soluble. This internal sac "vault" would then be housed by a saline filled middle silicone sac ("safety chamber") with both inner and outer membranes coated with the sterile beeswax preventing fluid gain or loss, maintaining the ideal weight of the implant and providing a tissue interface to prevent friction, weakening and rupture of the middle sac. To further minimize the potential of outer and inner sac rupture, the triple lumen implant adds yet another layer of safety. In particular, the middle saline sac is surrounded by a protective chamber ("insurance chamber") also filled with saline. Each sac of the three lumen implant is treated with the sterile beeswax as described above.

DESCRIPTION OF THE PREFERRED EMBODIMENTS

This device of the invention presents first and foremost to the implant market the safest and as close to an all natural implant known to date. Further, this new implant device incorporates multiple safety factors including a natural filler such as ultra-filtered honey, blue agave or aloe vera, which prevents the short and long term complications of silicone mastitis and other inflammatory reactions to foreign material substances or membranes introduced within the living tissues of the body and prevents autoimmune disorders from leakage of the implant's contents into the living tissues in the event of implant rupture. The new sac construction with a triple lumen adds an extra compartment and, capsular formation is prevented by coating the silicone sacs with sterile beeswax, which prevents direct contact of any part of the silicone sac with human tissue.

This device will prevent or greatly reduce the weakening of the implant wall from "sac fold" and resultant self-abrasion, because of the protective sterile beeswax coating on all inner and outer layers of the implant walls.

The device eliminates gel and fluid bleed because of the natural permanent coating of sterile beeswax on all layers of the multiple chambered sac.

The possibility of silicone mastitis and other inflammatory reactions is eliminated because there is no silicone or other type of unnatural chemical filler used. This also eliminates the possibility of autoimmune disorders associated with medical grade silicone, and eliminates the sac "crinkle" associated with approximately 90% of all saline implants available on the market today.

The implant of the invention has thereby best immediate cosmetic and long term appearance and feel because of the extreme flexibility and soft feel of the sterile beeswax melded into the inner and outer layers of the multi-chambered sac.

In the unlikely event of rupture, the implant offers the patient the reassurance that the filler contents are all able to be absorbed by the body, and are safe for body contact, honey being used worldwide for treatment of burns because of its anti-bacterial properties, and aloe being used both internally and externally to relieve multiple medical conditions. Because of the hygroscopic nature of honey, blue agave and aloe vera, all actually resist or prevent infection as opposed, for example, to an agar filler that is a medium for culture growth. The only potential bacterial problem with these fillers is the potential for harboring staphylococcus spores, and may be obviated by gamma radiation of the honey, blue agave and aloe vera before containment in the sac system.

Figure 1:
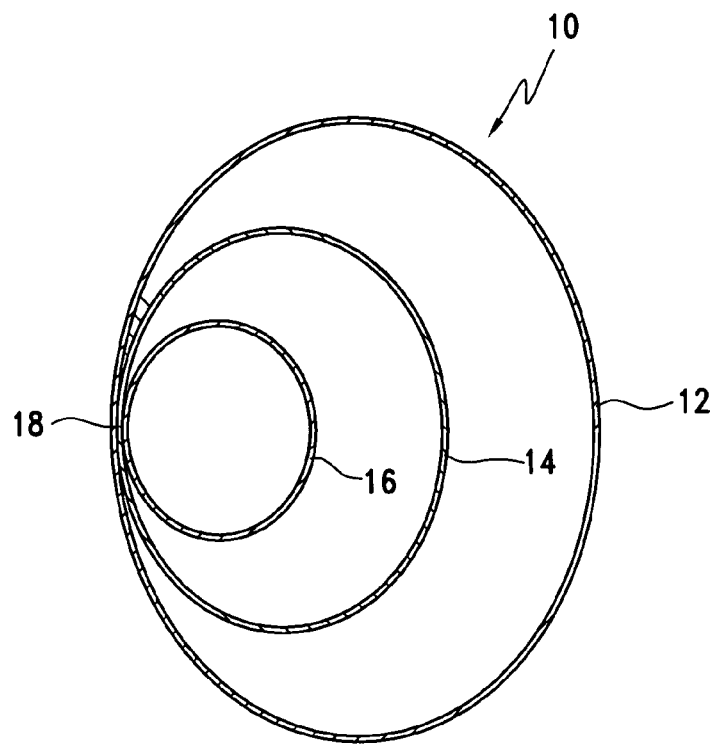
FIG. 1 is a cross-sectional side view of a first embodiment according to the invention.
Figure 1A:
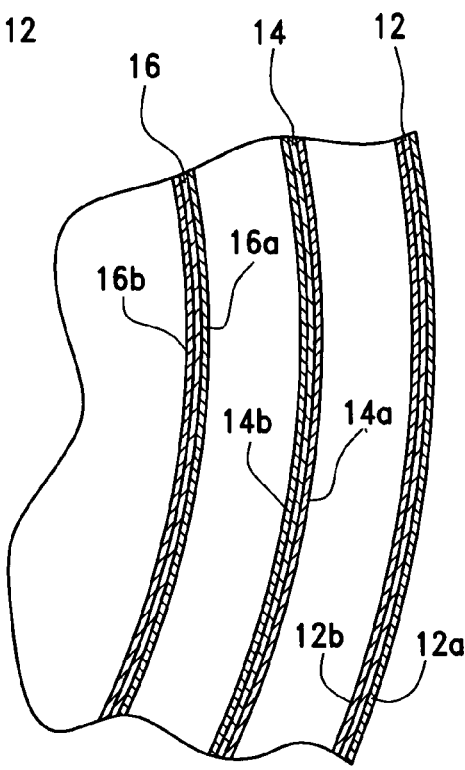
FIG. 1A is an enlarged view of a portion of FIG. 1.

In a first embodiment of the invention shown in FIG. 1, sac 10, shown in cross-section, includes an outer sac 12, an intermediate sac 14 and an inner sac 16. As shown in FIG. 1a, each of the surfaces of the sacs, 12a, 12b, 14a, 14b, 16a and 16b, is coated with beeswax. Inner sac 16 is filled with honey, agave or aloe, while sacs 12 and 14 are filled with saline solution. The sacs are joined by means known in the art at a point 18.

Figure 2:
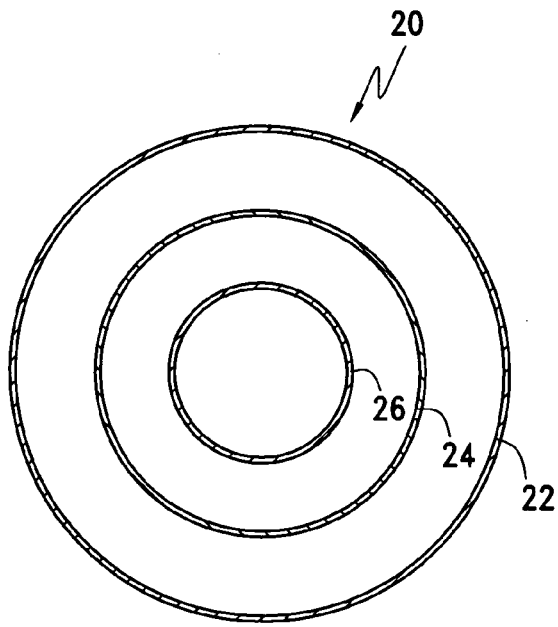
FIG. 2 is a cross-sectional side view of a second embodiment according to the invention.

It is also possible for all (or any two of the three) sacs to be free floating, and FIG. 2 shows an implant 20 where sacs 22, 24 and 26 float freely.

What is claimed is:

1. A human or animal implant device comprising a first, inner sealed silicone sheet sac, a second, intermediate sealed silicone sheet sac completely surrounding the first, inner sac, and a third, outer sealed silicone sheet sac completely surrounding the second sac, each sac having a coating of beeswax on inner and outer walls thereof, the first, inner sac being filled with a substantially sterile liquid material, and the second, intermediate sac and the third, outer sac being filled with aqueous saline solution.

2. The implant device of claim 1, wherein the sterile liquid material is selected from the group consisting of ultrafiltered honey, agave and aloe.

3. The implant device of claim 2, wherein the sterile liquid material has a viscosity of at least about 15 cp.

4. The implant device of claim 1, wherein the first, inner sac, the second, intermediate sac and the third, outer sac are not attached, and float freely with respect to each other.

5. The implant device of claim 1, wherein the first, inner sac is attached over a portion of the outer wall thereof to a portion of the inner wall of the second, intermediate sac.

6. The implant device of claim 1, wherein the second, intermediate sac is attached over a portion of the outer wall thereof to a portion of the inner wall of the third, outer sac.

7. The implant device of claim 1, wherein the beeswax coating is melded into the walls of each sac by dipping the silicone sheet into melted beeswax before sac formation.

8. The implant device of claim 1, wherein the beeswax coating on each wall has a thickness of about 0.01–1 mm.

\* \* \* \* \*